US012699359B2

(12) United States Patent
Gong et al.

(10) Patent No.: US 12,699,359 B2
(45) Date of Patent: Aug. 4, 2026

(54) SMART WATCH

(71) Applicant: GOERTEK INC., Shandong (CN)

(72) Inventors: Jiaqing Gong, Shandong (CN); Yong Qie, Shandong (CN)

(73) Assignee: GOERTEK INC., Shandong (CN)

( * ) Notice: Subject to any disclaimer, the term of this patent is extended or adjusted under 35 U.S.C. 154(b) by 860 days.

(21) Appl. No.: 17/907,469

(22) PCT Filed: Oct. 31, 2020

(86) PCT No.: PCT/CN2020/125630
§ 371 (c)(1),
(2) Date: Sep. 27, 2022

(87) PCT Pub. No.: WO2021/196598
PCT Pub. Date: Oct. 7, 2021

(65) Prior Publication Data
US 2023/0124396 A1     Apr. 20, 2023

(30) Foreign Application Priority Data

Mar. 30, 2020     (CN) .......................... 202010236819.3

(51) Int. Cl.
*A61B 5/00*          (2006.01)
*A61B 5/022*         (2006.01)
                     (Continued)

(52) U.S. Cl.
CPC ....... *G04G 21/025* (2013.01); *A61B 5/02233* (2013.01); *A61B 5/282* (2021.01); *A61B 5/681* (2013.01)

(58) Field of Classification Search
None
See application file for complete search history.

(56) References Cited

U.S. PATENT DOCUMENTS

2015/0173632 A1*   6/2015   Ma ..................... A61B 5/02438
                                                            600/324
2016/0161922 A1    6/2016   Shin
2019/0269914 A1*   9/2019   Moaddeb ............... A61B 5/369

FOREIGN PATENT DOCUMENTS

CN        103529684 A      1/2014
CN        106963351 A      7/2017
                    (Continued)

*Primary Examiner* — William J Levicky
*Assistant Examiner* — Anant A Gupta
(74) *Attorney, Agent, or Firm* — Ingrassia Fisher & Lorenz, LLP

(57) ABSTRACT

A smart watch comprises a watch head and a watch strap. The watch head comprises: a first electrode for contacting skin of a watch-wearing wrist; a second electrode for contacting skin of a non-watch-wearing wrist, wherein both the first electrode and the second electrode are electrically connected with a main control unit of the smart watch, so that the main control unit calculates an electrocardiogram according to bioelectric signals detected by the first electrode and the second electrode; and an air bag for contacting the skin of the watch-wearing wrist, wherein the air bag is respectively connected with an air pump and a pressure sensor, and the pressure sensor is connected with the main control unit, so that the main control unit calculates blood pressure according to a detection signal of the pressure sensor.

11 Claims, 4 Drawing Sheets

(51) Int. Cl.
　　 *A61B 5/282* 　　　　 (2021.01)
　　 *G04G 21/02* 　　　　 (2010.01)

(56) References Cited

FOREIGN PATENT DOCUMENTS

| CN | 207545156 U | | 6/2018 |
|---|---|---|---|
| CN | 208110294 U | | 11/2018 |
| CN | 209712887 U | | 12/2019 |
| CN | 110840463 A | | 2/2020 |
| CN | 210019307 U | * | 2/2020 |
| CN | 111387965 A | | 7/2020 |

* cited by examiner

41

4

53

5

51

54

SMART WATCH

CROSS-REFERENCE TO RELATED APPLICATION

This Application is a U.S. National-Stage entry under 35 U.S.C. § 371 based on International Application No. PCT/CN2020/125630, filed Oct. 31, 2020 which was published under PCT Article 21(2) and which claims priority to Chinese Application No. 202010236819.3, filed Mar. 30, 2020, which are all hereby incorporated herein in their entirety by reference.

TECHNICAL FIELD

This application pertains to the technical field of intelligent wearable devices, more specifically, to a smart watch.

BACKGROUND

With the increasing of cardiovascular related diseases, chronic disease management has become particularly important. In order to monitor the physiological condition of patients anytime and anywhere, more and more intelligent wearable products integrate the function of monitoring vital sign parameters, especially among which smart watches are favored by more and more chronic disease management patients because of their convenience.

For example, smart watches on the market at present include blood pressure detection smart watches and ECG (electrocardiogram) detection smart watches. Blood pressure detection smart watches usually use oscillographic technology to detect human blood pressure by adding blood pressure detection air bags to smart watches, while ECG detection smart watches use ECG technology to detect the ECG of the human body.

However, the smart watches in the prior art usually only have the function of monitoring one vital sign parameter, such as blood pressure or ECG. When chronic disease management patients need to detect both blood pressure and ECG, the existing smart watches cannot meet the multifunctional needs of chronic disease management patients.

Therefore, how to provide a smart watch that can detect both human blood pressure and ECG is an urgent problem for those skilled in the art. In addition, other objects, desirable features and characteristics will become apparent from the subsequent summary and detailed description, and the appended claims, taken in conjunction with the accompanying drawings and this background.

SUMMARY

In view of this, the object of the present disclosure is to provide a smart watch, which can not only detect the user's ECG, but also detect the user's blood pressure, so as to meet the needs of chronic disease management patients for multiple functions.

In order to achieve the above object, the present disclosure provides the following technical solutions.

A smart watch, comprising: a watch head and a watch strap, wherein the watch head comprises:

a first electrode for contacting skin of a watch-wearing wrist;

a second electrode for contacting skin of a non-watch-wearing wrist, wherein both the first electrode and the second electrode are electrically connected with a main control unit of the smart watch, so that the main control unit calculates an electrocardiogram according to bioelectric signals detected by the first electrode and the second electrode; and an air bag for contacting the skin of the watch-wearing wrist, wherein the air bag is respectively connected with an air pump and a pressure sensor, and the pressure sensor is connected with the main control unit, so that the main control unit calculates blood pressure according to a detection signal of the pressure sensor.

Preferably, the first electrode is connected with a back case of the watch head via a back cover of the watch head.

Preferably, the first electrode is provided with a stud, a first through hole and a second through hole are respectively provided on the back cover and the back case at positions corresponding to the stud, and the stud passes through the first through hole and the second through hole and is connected with the first fixing screw.

Preferably, the second electrode is a front case assembly of the watch head.

Preferably, the front case assembly is connected with the back case through a second fixing screw.

Preferably, the main control unit is arranged in the front case assembly.

Preferably, the air bag is an annular air bag, and an inner ring of the annular air bag is clamped between the back cover and the back case.

Preferably, the back case is provided with a positioning pin for positioning the air bag, and the air bag is provided with a third through hole for matching with the positioning pin.

Preferably, the air bag is provided with a first port for connecting with the air pump and a second port for connecting with the pressure sensor, and the back case is provided with a fourth through hole and a fifth through hole for passing through the first port and the second port respectively.

Preferably, a side of the air bag for contacting the skin of the watch-wearing wrist is provided with a number of grooves for increasing contact stability.

In the smart watch according to the present disclosure, the first electrode contacts the skin of the watch-wearing wrist, detects the bioelectric signal on the skin of the watch-wearing wrist, and transmits the bioelectric signal to the main control unit; when it needs to detect the user's ECG, the user can contact the skin of the non-watch-wearing wrist with the second electrode, so that the second electrode can detect the bioelectric signal on the skin of the non-watch-wearing wrist and transmit the bioelectric signal to the main control unit, and the ECG detection is realized through the calculation of the main control unit. In addition, the air bag is inflated by the air pump, the pressure of the air bag is detected by the pressure sensor, and the pressure of the air bag is transmitted to the main control unit, so that the main control unit can calculate the blood pressure according to the detection signal of the pressure sensor.

Therefore, the smart watch can not only detect the user's ECG, but also detect the user's blood pressure, so as to meet the needs of patients with chronic disease management for multiple functions. At the same time, the first electrode, the second electrode, the air bag, the air pump and the pressure sensor are all integrated into the watch head, so that the structure and material of the watch strap are not limited, and thus different watch straps can be flexibly selected to match with the watch head.

BRIEF DESCRIPTION OF DRAWINGS

The present invention will hereinafter be described in conjunction with the following drawing figures, wherein like numerals denote like elements, and.

Figure 1:
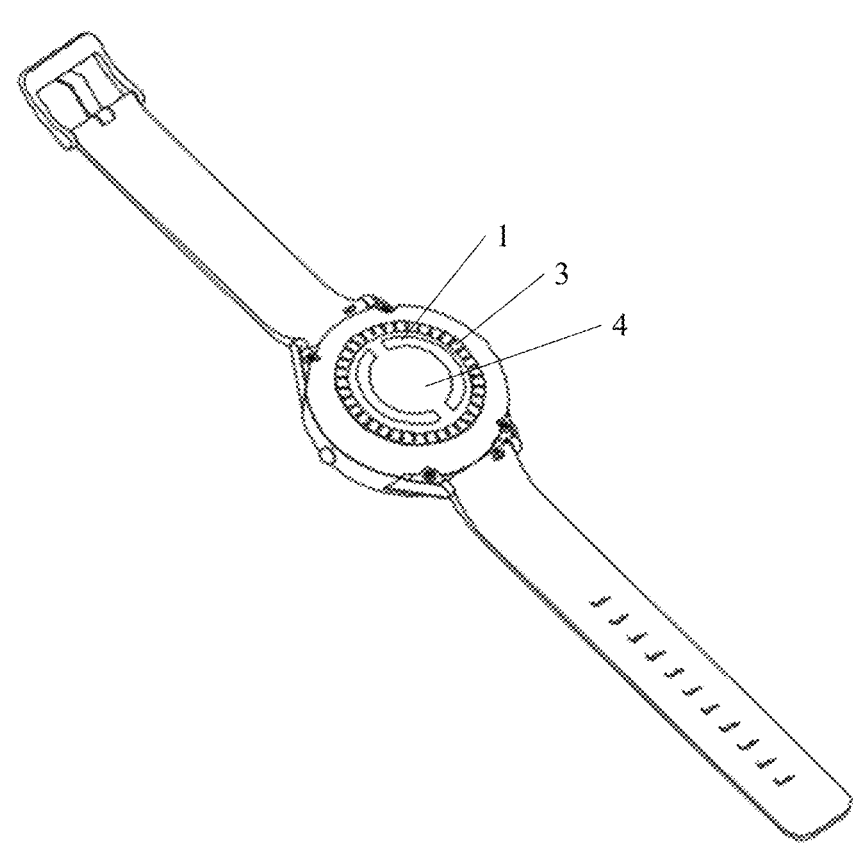
FIG. 1 is a schematic view of the structure of a smart watch according to a specific embodiment of the present disclosure.

The reference numerals in FIGS. 1 to 8 are as follows:

1, first electrode; 11, stud; 2, second electrode; 3, air bag; 31, third through hole; 32, first port; 33, second port; 34, groove; 4, back cover; 41, first through hole; 5, back case; 51, second through hole; 52, positioning pin; 53, fourth through hole; 54, fifth through hole; 6, first fixing screw; 7, front case assembly; 8, second fixing screw; 9, main control unit; 10, air pump; 12, pressure sensor.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

The technical solutions in embodiments of the present disclosure will be described clearly and completely below with reference to the drawings in the embodiments of the present disclosure. Obviously, the embodiments as described below are merely part of, rather than all, embodiments of the present disclosure. Based on the embodiments of the present disclosure, any other embodiment obtained by a person of ordinary skill in the art without paying any creative effort shall fall within the protection scope of the present disclosure.

The core of the present disclosure is to provide a smart watch, which can not only detect the user's ECG, but also detect the user's blood pressure, so as to meet the needs of chronic disease management patients for multiple functions.

Figure 2:
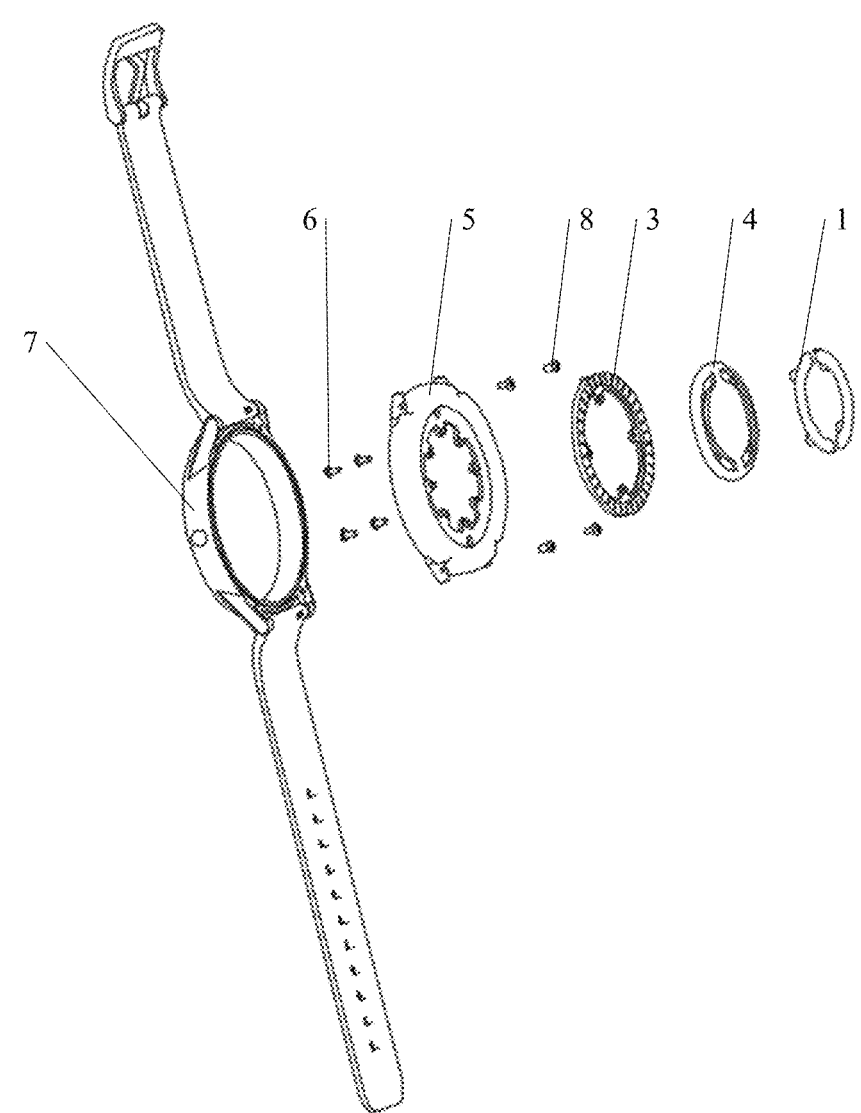
FIG. 2 is an exploded view of FIG. 1.
Figure 3:
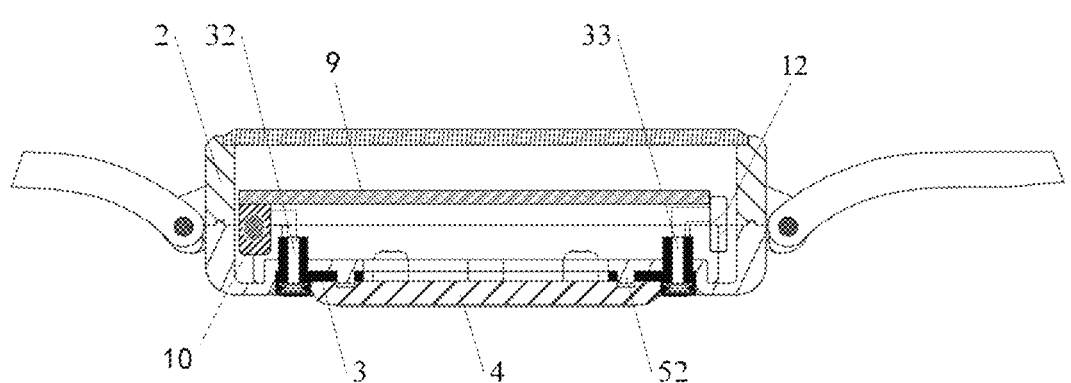
FIG. 3 is a sectional view of a watch head in FIG. 1.
Figure 4:
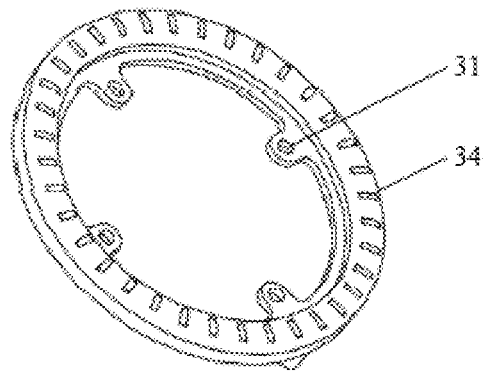
FIG. 4 is a schematic view of the structure of an air bag in FIG. 1.
Figure 5:
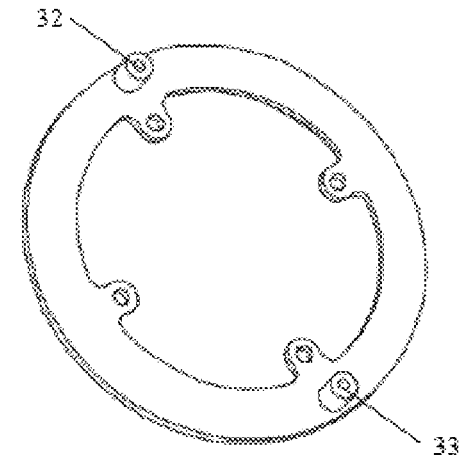
FIG. 5 is a schematic view of the structure of FIG. 4 from another viewing angle.
Figure 6:
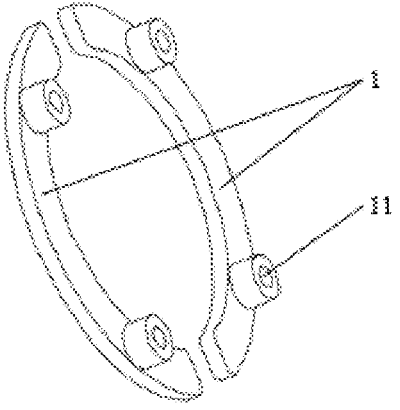
FIG. 6 is a schematic view of the structure of a first electrode in FIG. 1.
Figure 7:
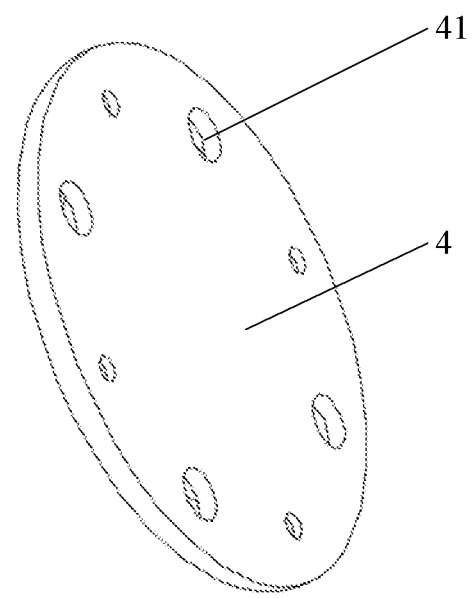
FIG. 7 is a schematic view of the structure of a back cover in FIG. 1.
Figure 8:
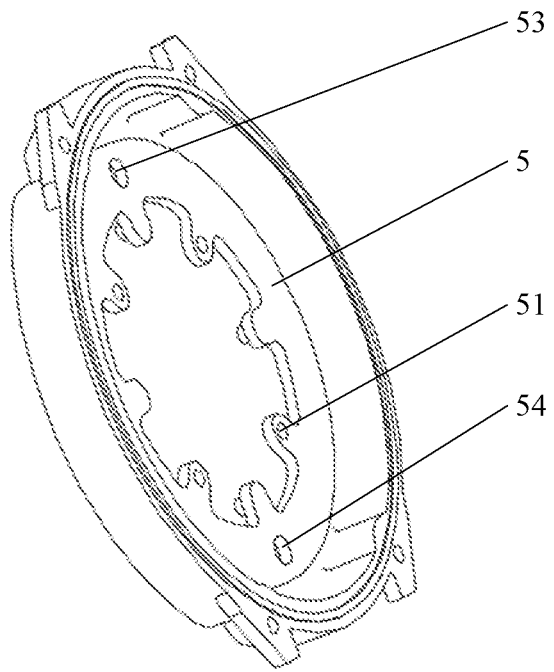
FIG. 8 is a schematic view of the structure of a back case in FIG. 1.

Please refer to FIG. 1 to FIG. 8. FIG. 1 is a schematic view of the structure of a smart watch according to a specific embodiment of the present disclosure; FIG. 2 is an exploded view of FIG. 1; FIG. 3 is a sectional view of a watch head in FIG. 1; FIG. 4 is a schematic view of the structure of an air bag in FIG. 1; FIG. 5 is a schematic view of the structure of FIG. 4 from another viewing angle; FIG. 6 is a schematic view of the structure of a first electrode; FIG. 7 is a schematic view of the structure of a back cover; and FIG. 8 is a schematic view of the structure of a back case.

The present disclosure provides a smart watch comprising a watch head and a watch strap. The watch head comprises a first electrode 1, a second electrode 2, an air bag 3, an air pump 10, a pressure sensor 12, etc.

Specifically, the first electrode 1 is configured to contact the skin of the watch-wearing wrist, the second electrode 2 is configured to contact the skin of the non-watch-wearing wrist, and both the first electrode 1 and the second electrode 2 are electrically connected with the main control unit 9 of the smart watch, so that the main control unit 9 can calculate the ECG according to the bioelectric signals detected by the first electrode 1 and the second electrode 2.

It should be noted that the watch-wearing wrist refers to the wrist of the user on which the smart watch is worn, and the non-watch-wearing wrist refers to the other wrist of the same user.

It can be understood that both the first electrode 1 and the second electrode 2 are made of conductive metals, such as stainless steel. After the user wears the smart watch, the first electrode 1 contacts the skin of the user's watch-wearing wrist, detects the bioelectric signal on the skin of the watch-wearing wrist, and transmits the bioelectric signal to the main control unit 9; when it needs to detect the user's ECG, the user can contact the skin of the non-watch-wearing wrist with the second electrode 2, so that the second electrode 2 can detect the bioelectric signal on the skin of the non-watch-wearing wrist and transmit the bioelectric signal to the main control unit 9, and the ECG detection is realized through the calculation of the main control unit 9.

The specific method of calculating the ECG, by the main control unit 9, based on the bioelectric signals detected by the first electrode 1 and the second electrode 2 is a mature technology and belongs to the prior art, which will not be repeated herein.

The specific method of calculating the ECG, by the main control unit, based on the bioelectric signals detected by the first electrode 1 and the second electrode 2 is a mature technology and belongs to the prior art, which will not be repeated herein.

Preferably, the first electrode 1 is an arc electrode.

Further preferably, the number of first electrodes 1 is two, and the two first electrodes 1 are arranged to face each other, as shown in FIG. 6.

In other words, by increasing the number of the first electrode 1, the first electrode 1 can form a redundant design to improve the reliability and performance scalability of the smart watch.

In addition, the air bag 3 is configured to contact the skin of the watch-wearing wrist, and the air bag 3 is connected with the air pump 10 to realize the inflation and deflation of the air bag 3 via the air pump 10. At the same time, the air bag 3 is connected with the pressure sensor 12 to detect the pressure of the air bag 3 via the pressure sensor 12, and the pressure of the air bag 3 is transmitted to the main control unit 9 via the pressure sensor 12, so that the main control unit 9 can calculate the blood pressure according to the detection signal of the pressure sensor 12.

It can be understood that when the user's blood pressure is detected, the air pump 10 inflates the air bag 3 to make the air bag 3 exert pressure on the watch-wearing wrist to squeeze the blood vessel. At this point, the blood in the blood vessel slowly stops flowing. When the pressure in the air bag 3 reaches a certain value, the air bag 3 stops inflating and slowly deflates. As the pressure in the air bag 3 continues to decrease, the blood flows in the blood vessel and has a certain oscillation wave which makes the pressure in the air bag 3 fluctuate. The pressure fluctuation of the air bag 3 is detected by the pressure sensor 12, and the main control unit 9 detects the user's blood pressure based on the oscillographic method. The detection of the human blood pressure using the oscillographic method is a mature technology in the prior art, which will not be repeated herein.

It can be seen that the smart watch according to the present disclosure can not only detect the user's ECG, but also detect the user's blood pressure, thereby meeting the needs of chronic disease management patients for multiple functions.

It should be noted that the first electrode 1, the second electrode 2, the air bag 3, the air pump 10 and the pressure sensor 12 are all integrated into the watch head, so that the structure and material of the watch strap are not limited, and thus different watch straps can be flexibly selected to match with the watch head.

The present disclosure does not specifically limit the specific positions and relative position relationship of the first electrode 1, the second electrode 2, the air bag 3, the air pump 10 and the pressure sensor 12.

Considering the convenience of arranging the first electrode 1, on the basis of the above embodiment, the first electrode 1 is connected with the back case 5 of the watch head via the back cover 4 of the watch head.

In other words, the first electrode 1 is arranged on the outside of the back cover 4 and faces the skin of the user's watch-wearing wrist so as to contact and fit the skin of the user's watch-wearing wrist.

Considering the user's comfort, preferably, the back cover 4 is provided with a sink for accommodating the first electrode 1. During installation, the first electrode 1 is placed in the sink so that the surface of the first electrode 1 is flush with the surface of the back cover 4.

Regarding the specific connection mode of the first electrode 1, the back cover 4 and the back case 5, as a preferred way, on the basis of the above embodiment, the first electrode 1 is provided with a stud 11, a first through hole 41 and a second through hole 51 are respectively provided on the back cover 4 and the back case 5 at positions corresponding to the stud 11, and the stud 11 passes through the first through hole 41 and the second through hole 51 and is connected with the first fixing screw 6.

In other words, the stud 11 is provided with an internal thread to be connected with the first fixing screw 6. When the stud 11 passes through the first through hole 41 and the second through hole 51 and is tightened with the first fixing screw 6, the connection of the first electrode 1, the back cover 4 and the back case 5 can be realized.

It should be noted that this embodiment does not limit the specific number of studs 11, as long as the first electrode 1, the back cover 4 and the back case 5 can be fixedly connected.

Preferably, the number of studs 11 is four. It can be understood that the numbers of the first through holes 41, the second through holes 51 and the first fixing screws 6 are the same as that of the studs 11, and there is one-to-one correspondence among the stud 11, the first through hole 41 and the second through hole 51.

Considering the convenience of arranging the second electrode 2, on the basis of the above embodiment, the second electrode 2 is a front case assembly 7 of the watch head.

In other words, in this embodiment, the entire front case assembly 7 is designed as the second electrode 2 so that the skin of the user's non-watch-wearing wrist contacts the second electrode 2.

Preferably, the front case assembly 7 is a structure that is processed and formed integrally.

Considering the convenience of connecting the front case assembly 7 and the back case 5, on the basis of the above embodiment, the front case assembly 7 and the back case 5 are connected via a second fixing screw 8.

In this embodiment, the specific number of the second fixing screws 8 is not limited. Preferably, the number of the second fixing screws 8 is four.

It should be noted that the present disclosure does not limit the specific position of the main control unit 9. Considering the convenience of arranging the main control unit 9, on the basis of the above embodiment, the main control unit 9 is arranged in the front case assembly 7.

In other words, the main control unit 9 is integrated into the watch head via the front case assembly 7 to facilitate the connection of the main control unit 9 with the first electrode 1, the second electrode 2 and the pressure sensor 12 respectively.

Considering the specific arrangement mode of the air bag 3, on the basis of the above embodiment, the air bag 3 is an annular air bag, and the inner ring of the annular air bag is clamped between the back cover 4 and the back case 5.

In other words, the radius of the inner ring of the annular air bag is less than the radius of the back cover 4, so that the annular air bag can be clamped and fixed via the fixation of the back cover 4 and the back case 5. At the same time, the radius of the outer ring of the annular air bag is greater than that of the back cover 4, so that the annular air bag can be exposed, so that when the annular air bag is inflated, it can contact the skin of the user's watch-wearing wrist.

It can be seen that in this embodiment, the air bag 3 is designed as an annular air bag, and the inner ring of the annular air bag is clamped between the back cover 4 and the back case 5, so that the first electrode 1 and the back cover 4 are located at the center of the annular air bag, which undoubtedly saves the space in the structure and makes the structure of the smart watch compact.

In order to avoid dislocation of the air bag 3 during use, on the basis of the above embodiment, the back case 5 is provided with a positioning pin 52 for positioning the air bag 3, and the air bag 3 is provided with a third through hole 31 for matching with the positioning pin 52.

In other words, in this embodiment, the positioning of the air bag 3 is realized through the cooperation of the positioning pin 52 and the third through hole 31, so that the relative position of the air bag 3 and the back case 5 remains unchanged.

In this embodiment, the specific number of positioning pins 52 is not limited, as long as the positioning of air bag 3 can be realized. Preferably, the number of positioning pins 52 is four; correspondingly, the number of the third through holes 31 is four, and the third through holes 31 and the positioning pins 52 are arranged with a one-to-one correspondence.

Considering the convenience of connecting the air bag 3 with the air pump 10 and the pressure sensor 12 respectively, on the basis of the above embodiment, the air bag 3 is provided with a first port 32 for connecting with the air pump 10 and a second port 33 for connecting with the pressure sensor 12, and the back case 5 is provided with a fourth through hole 53 and a fifth through hole 54 through which the first port 32 and the second port 33 pass respectively.

Preferably, the air pump 10 and the pressure sensor 12 are both arranged in the front case assembly 7, and the first port 32 is connected with the air pump 10 after passing through the fourth through hole 53, and the second port 33 is connected with the pressure sensor 12 after passing through the fifth through hole 54.

On the basis of the above embodiment, a side of the airbag 3 for contacting the skin of the watch-wearing wrist is provided with a number of grooves 34 to increase the contact stability.

This embodiment does not limit the shape and specific number of grooves 34.

Preferably, all grooves 34 are uniformly distributed along the circumferential direction of the air bag 3.

It should be noted that in the above embodiments, the main body structures of the back cover 4, the back case 5 and the front case assembly 7 of the watch head may refer to the prior art respectively, and are not specifically limited herein.

It should also be noted that in this specification, relational terms such as first and second are only used to distinguish one entity or operation from another entity or operation, and do not necessarily require or imply any actual relationship or order between these entities or operations.

Each embodiment in this specification is described in a progressive manner, and focuses on the differences from other embodiments. The same and similar parts of the embodiments can refer to each other.

The above describes the smart watch according to the present disclosure in detail. Herein, specific examples are used to explain the principle and implementation mode of the present disclosure. The description of the above examples is only used to help understand the method and core idea of the present disclosure. It should be noted that, for those skilled in the art, various improvements and modifications can be made to the present disclosure without departing from the principles of the present disclosure, and these improvements and modifications shall fall within the protection scope of the claims of the present disclosure.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. A smart watch, comprising: a watch head and a watch strap, wherein the watch head comprises:
   a first electrode (1) configured for contacting skin of a watch-wearing wrist;
   a second electrode (2) configured for contacting skin of a non-watch-wearing wrist, wherein both the first electrode (1) and the second electrode (2) are electrically connected with a main control unit of the smart watch, so that the main control unit calculates an electrocardiogram according to bioelectric signals detected by the first electrode (1) and the second electrode (2); and
   an air bag (3) configured for contacting the skin of the watch-wearing wrist, wherein the air bag (3) is respectively connected with an air pump and a pressure sensor, and the pressure sensor is connected with the main control unit, so that the main control unit calculates blood pressure according to a detection signal of the pressure sensor,
   wherein the first electrode (1) is connected with a back case (5) of the watch head via a back cover (4) of the watch head, and
   wherein the first electrode (1) is provided with a stud (11), a first through hole (41) and a second through hole (51) are respectively provided on the back cover (4) and the back case (5) at positions corresponding to the stud (11), and the stud (11) passes through the first through hole (41) and the second through hole (51) and is connected with a first fixing screw (6).

2. The smart watch according to claim 1, wherein the second electrode (2) is a front case assembly (7) of the watch head.

3. The smart watch according to claim 1, wherein the front case assembly (7) is connected with the back case (5) through a second fixing screw (8).

4. The smart watch according to claim 2, wherein the main control unit is arranged in the front case assembly (7).

5. The smart watch according to claim 1, wherein the air bag (3) is an annular air bag, and an inner ring of the annular air bag is clamped between the back cover (4) and the back case (5).

6. The smart watch according to claim 5, wherein the back case (5) is provided with a positioning pin (52) configured for positioning the air bag (3), and the air bag (3) is provided with a third through hole (31) configured for matching with the positioning pin (52).

7. The smart watch according to claim 5, wherein the air bag (3) is provided with a first port (32) configured for connecting with the air pump and a second port (33) configured for connecting with the pressure sensor, and the back case (5) is provided with a fourth through hole (53) and a fifth through hole (54) through which the first port (32) and the second port (33) pass respectively.

8. The smart watch according to claim 5, wherein a side of the air bag (3) configured for contacting the skin of the watch-wearing wrist is provided with a number of grooves (34) for increasing contact stability.

9. The smart watch according to claim 2, wherein the air bag (3) is an annular air bag, and an inner ring of the annular air bag is clamped between the back cover (4) and the back case (5).

10. The smart watch according to claim 3, wherein the air bag (3) is an annular air bag, and an inner ring of the annular air bag is clamped between the back cover (4) and the back case (5).

11. The smart watch according to claim 4, wherein the air bag (3) is an annular air bag, and an inner ring of the annular air bag is clamped between the back cover (4) and the back case (5).

* * * * *